United States Patent [19]

Teach

[11] 4,119,636
[45] Oct. 10, 1978

[54] PREPARATION OF ACYCLIC AND ALICYCLIC N-SUBSTITUTED HALO-2-PYRROLIDINONES

[75] Inventor: Eugene G. Teach, El Cerrito, Calif.

[73] Assignee: Stauffer Chemical Company, Westport, Conn.

[21] Appl. No.: 829,396

[22] Filed: Aug. 31, 1977

Related U.S. Application Data

[60] Division of Ser. No. 647,962, Jan. 9, 1976, and a continuation-in-part of Ser. No. 563,280, Mar. 28, 1975, abandoned.

[51] Int. Cl.$^2$ ............................................. C07D 207/38
[52] U.S. Cl. ............................................. 260/326.5 FL
[58] Field of Search ............................... 260/326.5 FL

[56] References Cited

U.S. PATENT DOCUMENTS 3,488,732  1/1970  Heiba et al. .................. 260/326.5 FL Primary Examiner—Paul M. Coughlan, Jr.
Assistant Examiner—Mark L. Berch
Attorney, Agent, or Firm—Harry A. Pacini

[57] ABSTRACT

Acyclic and alicyclic N-substituted halo-2-pyrrolidinones having the formula

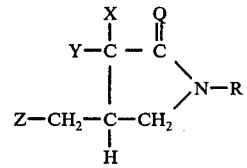

in which Q is oxygen or sulfur; R is lower alkyl, haloalkyl, alkenyl, cycloalkyl, cycloalkylalkyl, benzyl and chlorobenzyl; X is hydrogen or chlorine, Y is chlorine or bromine and Z is chlorine or bromine, provided that when R is allyl, Y and Z are each chlorine or bromine, and provided that when R is cyclohexyl, X is other than chlorine. The compounds of this invention are prepared by a novel process and are useful as herbicides.

6 Claims, No Drawings

PREPARATION OF ACYCLIC AND ALICYCLIC N-SUBSTITUTED HALO-2-PYRROLIDINONES

This is a division, of application Ser. No. 647,962, filed Jan. 9, 1976, pending and a continuation-in-part application of copending application Ser. No. 563,280, filed Mar. 28, 1975, now abandoned.

This invention relates to certain novel N-substituted halo-2-pyrrolidinones (also known as azacyclopentan-3-ones) which are prepared by a novel process and which are useful as herbicides. More specifically, this invention relates to certain acyclic and alicyclic N-substituted halo-2-pyrrolidinones, to their preparation and utility of the compounds as herbicides.

The compound comprising the instant class of compounds correspond to the general formula:

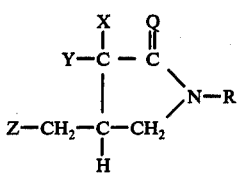

in which Q is oxygen or sulfur; R is lower alkyl, alkenyl, haloalkyl, cycloalkyl, cycloalkylalkyl, benzyl and chlorobenzyl; X is hydrogen or chlorine; Y is chlorine or bromine, and Z is chlorine or bromine; provided that when R is allyl, Y and Z are each chlorine or bromine, and provided that when R is cyclohexyl, X is other than chlorine.

In the above description, the following preferred embodiments are intended for the various substituent groups: Lower alkyl preferably includes, unless otherwise provided for, those members which contain from 1 to 6 carbon atoms, inclusive, in both straight chain and branched chain configurations, for example, methyl, ethyl, n-propyl, isopropyl, n-butyl, isobutyl, amyl, isoamyl, hexyl and isohexyl, and the like; by the term "haloalkyl" is meant those previously described alkyl members having 1 to 6 carbon atoms, having in addition one or more halogen substitutions such as mono, di, tri, tetra and per fluoro, chloro, bromo or iodo; alkenyl preferably includes, unless otherwise provided for, those members which contain at least one olefinic double bond and contains from 3 to 6 carbon atoms, inclusive; for example, allyl, methallyl, ethallyl, 1-butenyl, 3-butenyl, 2-methyl-1-butenyl, 1-pentenyl, 2-pentenyl, 3-pentenyl, 2-methyl-1-pentenyl, 1-hexenyl, 2-hexenyl, 3-hexenyl and the like; cycloalkyl preferably includes from 3 to 7 carbon atoms, inclusive, for example, cyclopropyl, cyclobutyl, cyclopentyl, cyclohexyl and the like; cycloalkylalkyl preferably includes those members having a total carbon content of from 4 to 8 carbon atoms, inclusive, including for example, cyclopropylmethyl, cyclopropylethyl, cyclobutylmethyl, cyclopentylmethyl, cyclohexylmethyl and the like.

As a consequence of the presence of unsymmetrically substituted carbon centers in certain of the compounds within the scope of this invention, it is recognized that the possibility exists for cis-trans or geometric isomerism. Such cis-trans isomers are stereoisomers whose structures differ only with respect to the arrangement of certain "rigidly" positioned atoms or groups relative to a specified plane of reference. The plane of reference herein is the pyrrolidinone ring. In specifying cis-trans configurations in a monocyclic compound, any of the ring positions having non-identical groups are considered to assign relative configurations. Using the pictoral connotation for representing these relative positions in structural formulas, the pyrrolidinone ring system is considered flat. The atoms or groups under consideration are described as cis when they are on the same side of the plane and trans when they are on opposite sides of the plane (see Gilman's, Organic Chemistry, Vol. I, p. 477).

The compounds of this invention have been found to be active herbicides of a general type. That is, members of the class have been found to be herbicidally effective against a wide range of plant species. A method of controlling undesirable vegetation of the present invention comprises applying an herbicidally effective amount of the above-described compounds to the area or plant locus where control is desired.

An herbicide is used herein to mean a compound which controls or modifies the growth of plants. By a "growth controlling amount" is meant an amount of compound which causes a modifying effect upon the growth of plants. Such modifying effects include all deviations from natural development, for example, killing, retardation, defoliation, desiccation, regulation, stunting, tillering, stimulation, dwarfing and the like. By "plants", it is meant germinant seeds, emerging seedlings, and established vegetation, including the roots and above-ground portions.

The intermediates for the preparation of the N-substituted halo-2-pyrrolidinones are the unsaturated haloacyl amides obtained by the acylation of the appropriate unsaturated amines. Unsaturated amines, that are not commercially available, may be prepared by methods reported in various sources of the chemical literature and various reviews on the subject such as "Synthetic Organic Chemistry" by Wagner and Zook, Chapter 24, John Wiley and Sons, New York, 1961. In the examples to follow, a specific example of the preparation of an intermediate unsaturated haloacyl amide is described.

The acyclic and alicyclic N-substituted halo-2-pyrrolidinones are prepared by several different methods, depending upon the nature of the starting materials and products desired. A preferred method not heretofore disclosed or known in the prior art is the rearrangement reaction of an N-alkenyl containing haloacetamide in the presence of a catalytic amount of ferrous ion. The use of a solvent is desirable to facilitate processing of the reaction and to aid in the agitation by providing adequate volumen, as well as solubilizing the reagents. The preferred solvents include those which are high boiling and which do not interfere with the reaction, for example, diethylene glycol dimethyl ether, dimethyl formamide, dimethyl acetamide, dimethylsulfoxide, mesitylene and the like. Ferrous ion catalyst sources may be provided from various reagents, for example, ferrous chloride, ferrous bromide, iron metal, ferrocene, ferrous acetonyl acetonate and the like.

Since the reaction is a rearrangement of the unsaturated haloacylamide in the presence of a catalytic amount of ferrous ion, the amounts of reagents is not critical. The reaction is preferably conducted at reflux temperatures. The temperatures for the reaction are best defined between about room temperature and the reflux temperature for the solvent if one is employed. Preferably, the reaction temperature is between about 50° C. to about 190° C., more preferably, the temperature range is between about 125° C. to about 170° C. At the elevated temperatures, the reaction as described hereinabove proceeds rapidly to yield the desired product. In each instance after the reaction is complete, the recovery is carried out by normal work-up procedures, such as crystallization, sublimation, distillation and the like.

Generally, the reaction can be represented by the following equation:

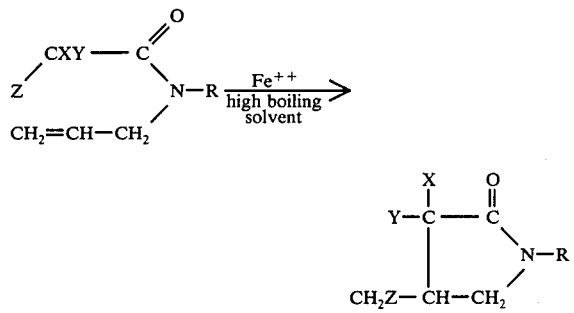

wherein X, Y, Z and R are defined as above.

The compounds of the present invention and intermediates therefor are more particularly illustrated by the following examples which describe their preparation. Following the examples is a table of compounds which are prepared according to the procedures described herein.

EXAMPLE A

Preparation of Intermediate N-allyl-N-butyl dichloroacetamide from allyl-n-butyl amine.

Allyl-n-butyl amine preparation. Fifty grams of N-allyl butyramide, prepared by the reaction of allyl amine with butyryl chloride, was dissolved in 100 ml. of benzene and admitted dropwise to a stirred solution of 168 g. of sodium bis(2-methoxy ethoxy) aluminum hydride (Red Al) ® in 300 ml. of benzene at reflux under a nitrogen atmosphere. Reflux was maintained for an hour after addition was complete after which the mixture was cooled and added dropwise to a solution prepared from 200 ml. of 50 percent sodium hydroxide and 300 g. of crushed ice. The aqueous layer was extracted with three 100 ml. portions of benzene and the combined benzene extracts were dried over magnesium sulfate and the product converted to the hydrochloride with excess 20 percent ethereal hydrochloric acid. The hydrochloride salt was filtered off and dried. Yield was 35.4 g. and the salt was used without further purification.

N-allyl-N-butyl dichloroacetamide preparation. Ten and five-tenths grams of allyl-n-butyl amine hydrochloride was added to 100 ml. of methylene chloride followed by 14.5 g. of triethylamine. The mixture was stirred in a water bath at room temperature while 10.4 g. of dichloroacetyl chloride was added dropwise, and stirring was continued for 30 minutes after addition was complete. The mixture was washed and the solvent stripped under vacuum. Yield was 13 g., $n_D^{30}$ 1.4603. The intermediate was used without further purification to prepare Compound No. 12 (Example VII).

EXAMPLE I

Preparation of N-allyl-3-chloro-4-chloromethyl-2-pyrrolidinone

Twenty and eight-tenths grams of N,N-diallyl dichloroacetamide was mixed with 25 g. of diethylene glycol dimethyl ether (diglyme), 1 g. of ferrous chloride (FeCl$_2$.4H$_2$O) added and the mixture was heated at reflux for 30 minutes. The conversion was monitored by the appearance of a new carbonyl peak at ~5.8 microns in the infrared. An additional gram of ferrous chloride (FeCl$_2$.4H$_2$O) was added and heating was continued for an additional 30 minutes. The reaction mixture was diluted with methylene chloride, washed with water and dried and stripped. The dark liquid product was distilled under vacuum to give 8.4 g. of light yellow oil, b.p. 124°–127° C. at 0.25 mm. $n_D^{30}$ 1.4850.

The proton and carbon-13 NMR spectra indicate that the product is a mixture of cis and trans isomers with a ratio of 2:1, cis to trans.

EXAMPLE II

Preparation of 1-allyl-3-bromo-4-bromomethyl-2-pyrrolidinone

Ten and nine-tenths grams of N,N-diallyl-dibromoacetamide was added to 15 ml. of diglyme followed by 1 g. of anhydrous ferrous bromide. The mixture was heated at reflux and the conversion to pyrrolidinone checked by GLPC. When conversion was complete, the product was diluted with methylene chloride, washed with water, dried over anhydrous magnesium sulfate and treated with silica gel to remove tarry material. The solvent was stripped under vacuum to give 8.1 g. of product, $n_D^{30}$ 1.5350.

EXAMPLE III

Preparation of N-allyl-3-chloro-4-chloromethyl-2-pyrrolidinonethione

Six and two-tenths grams of N-allyl-3-chloro-4-chloromethyl-2-pyrrolidinone was dissolved in 100 ml. of methylene chloride and 10 g. of phosphorus pentasulfide in two 5 gram portions was added about an hour apart while the mixture was allowed to stir at room temperature overnight. The mixture was filtered to remove solids and stripped to give 5 g. of liquid containing some precipitated solid. This was taken up in pentane, filtered to remove solids and stripped. There was obtained 3 g. of the product, an oil, $n_D^{30}$ 1.5487. Examination of the infrared spectrum showed almost no carbonyl absorption at ~5.8 microns.

EXAMPLE IV

Preparation of N-propyl-3-chloro-4-chloromethyl-2-pyrrolidinone

This compound can be prepared by the rearrangement of N-allyl-N-propyl dichloro acetamide or by reduction of N-allyl-3-chloro-4-chloromethyl-2-pyrrolidinone as shown below.

Twenty and eight-tenths grams of N-allyl-3-chloro-4-chloromethyl-2-pyrrolidinone was dissolved in 150 ml. of ethanol and 150 mg. platinum oxide was added. The mixture was shaken under hydrogen gas at 48 psi until hydrogen uptake was complete (22 minutes). The mixture was treated with a few grams of Dicalite and filtered to remove the catalyst and the solvent stripped under vacuum. Yield was 21 g. of product, $n_D^{30}$ 1.4748.

EXAMPLE V

Preparation of N-benzyl-3-chloro-4-chloromethyl-2-pyrrolidinone

Eleven and one-tenth grams of N-allyl-N-benzyl dichloroacetamide was dissolved in 12 ml. of diglyme and 1 g. of anhydrous ferrous chloride added. The mixture was heated at reflux under nitrogen until conversion to the pyrrolidinone was complete as indicated by GLPC. The mixture was diluted with methylene chloride, washed with 5 percent hydrochloric acid, separated, dried over anhydrous magnesium sulfate, treated with activated carbon and Florisil and stripped under vacuum. Yield was 6 g. of the title compound, $n_D^{30}$ 1.5387.

EXAMPLE VI

Preparation of N-cyclopropylmethyl-3-chloro-4-chloromethyl-2-pyrrolidinone

Twelve and one-tenth grams of N-allyl-N-cyclopropylmethyl dichloroacetamide was dissolved in 15 ml. of diglyme and 1 g. of anhydrous ferrous chloride added. The mixture was heated at reflux under a nitrogen atmosphere for 25 minutes and conversion checked by GLPC. When conversion was complete, the diglyme was stripped off under vacuum and the mixture dissolved in benzene, washed with 5 percent hydrochloric acid, separated, dried over anhydrous magnesium sulfate, treated with activated carbon, filtered through Florisil and the solvent removed under vacuum. Yield was 8.8 g. of product, $n_D^{30}$ 1.4922.

EXAMPLE VII

Preparation of N-butyl-3-chloro-4-chloromethyl-2-pyrrolidinone

Eleven grams of N-allyl-N-butyl dichloroacetamide was dissolved in 15 ml. of diglyme and 1 g. of anhydrous ferrous chloride was added. The mixture was heated to reflux in a nitrogen atmosphere for 25 minutes and the conversion monitored by gas-liquid partition chromatograph (GLPC). The diglyme was stripped off under vacuum and the mixture diluted with benzene, washed with 5 percent hydrochloric acid, dried over anhydrous magnesium sulfate and treated with activated carbon to remove tarry by-products and filtered through Florisil. The solvent was stripped under vacuum to give 8.1 g. of product, $n_D^{30}$ 1.4731.

The following is a table of compounds which are prepared according to the aforementioned procedures. Compound numbers have been assigned to them and are used for identification throughout the balance of the specification.

TABLE I

| Compound Number | R | X | Y | Z | Q | $n_D^{30}$ or b.p. ° C. |
|---|---|---|---|---|---|---|
| 1 | $CH_2=CH_2$ | H | Cl | Cl | O | 125°/0.25 mm. |
| 2 | $CH_2CH=CH_2$ | Cl | Cl | Cl | O | 1.4938 |
| 3 | $C_2H_5$ | H | Cl | Cl | O | 1.4720 |
| 4 | $C_2H_5$ | Cl | Cl | Cl | 0 | 1.4735 |
| 5 | $c\text{-}C_6H_{11}$ | H | Cl | Cl | O | 1.4788 |
| 6 | $CH_2CH=CH_2$ | H | Cl | Cl | S | 1.5487 |
| 7 | $CH_3$ | H | Cl | Cl | O | 1.4860 |

TABLE I-continued

| Compound Number | R | X | Y | Z | Q | $n_D^{30}$ or b.p. ° C. |
|---|---|---|---|---|---|---|
| 8 | $n\text{-}C_3H_7$ | H | Cl | Cl | O | 1.4748 |
| 9 | $CH_2=CHCH_2$ | H | Br | Br | O | 1.5350 |
| 10 | $CH_2BrCHBrCH_2$ | H | Cl | Cl | O | 1.5633 |
| 11 | $n\text{-}C_5H_{11}$ | H | Cl | Cl | O | 1.4700 |
| 12 | $n\text{-}C_4H_9$ | H | Cl | Cl | O | 1.4731 |
| 13 | $i\text{-}C_4H_9$ | H | Cl | Cl | O | 1.4720 |
| 14 | ▷—$CH_2$ | H | Cl | Cl | O | 1.4922 |
| 15 | $C_6H_5CH_2$ | H | Cl | Cl | O | 1.5387 |
| 16 | $p\text{-}Cl\text{-}C_6H_5CH_2$ | H | Cl | Cl | O | 1.5502 |

The foregoing compounds may be designated:
1. 1-allyl-3-chloro-4-chloromethyl-2-pyrrolidinone
2. 1-allyl-3,3-dichloro-4-chloromethyl-2-pyrrolidinone
3. 1-ethyl-3-chloro-4-chloromethyl-2-pyrrolidinone
4. 1-ethyl-3,3-dichloro-4-chloromethyl-2-pyrrolidinone
5. 1-cyclohexyl-3-chloro-4-chloromethyl-2-pyrrolidinone
6. 1-allyl-3-chloro-4-chloromethyl-2-pyrrolidinonethione
7. 1-methyl-3-chloro-4-chloromethyl-2-pyrrolidinone
8. 1-propyl-3-chloro-4-chloromethyl-2-pyrrolidinone
9. 1-allyl-3-bromo-4-bromomethyl-2-pyrrolidinone
10. N-2,3-dibromopropyl-3-chloro-4-chloromethyl-2-pyrrolidinone
11. N-amyl-3-chloro-4-chloromethyl-2-pyrrolidinone
12. N-butyl-3-chloro-4-chloromethyl-2-pyrrolidinone
13. N-isobutyl-3-chloro-4-chloromethyl-2-pyrrolidinone
14. N-cyclopropylmethyl-3-chloro-4-chloromethyl-2-pyrrolidinone
15. N-benzyl-3-chloro-4-chloromethyl-2-pyrrolidinone
16. N-p-chlorobenzyl-3-chloro-4-chloromethyl-2-pyrrolidinone

HERBICIDAL SCREENING TESTS

As previously mentioned, the herein described compounds produced in the above-described manner are phytotoxic compounds which are useful and valuable in controlling various plant species. Compounds of this invention are tested as herbicides in the following manner.

PRE-EMERGENCE HERBICIDE SCREENING TEST

Using an analytical balance, 20 mg. of the compound to be tested is weighed out on a piece of glassine weighing paper. The paper and compound are placed in a 30 ml. wide-mouth bottle and 3 ml. of acetone containing 1% Tween 20 ® (polyoxyethylene sorbitan monolaurate) is added to dissolve the compound. If the material is not soluble in acetone, another solvent such as water, alcohol or dimethylformamide (DMF) is used instead. When DMF is used, only 0.5 ml. or less is used to dissolve the compound and then another solvent is used to make the volume up to 3 ml. The 3 ml. of solution is sprayed uniformly on the soil contained in a small flat one day after planting weed seeds in the flat of soil. An atomizer is used to apply the spray using compressed air at a pressure of 5 lb./sq. inch. The rate of application is 8 lb./acre and the spray volume is 143 gallons per acre.

On the day preceding treatment, the flat which is 7 inches long, 5 inches wide and 2.75 inches deep, is filled to a depth of 2 inches with loamy sand soil. Seeds of seven different weed species are planted in individual rows using one species per row across the width of the flat. The seeds are covered with soil so that they are planted at a depth of 0.5 inch. Ample seeds are planted to give about 20 to 50 seedlings per row after emergence depending on the size of the plants.

The seeds used are foxtail (*Setaria spp.*) - FT; watergrass (*Echinochloa crusgalli*) - WG; red oat (*Avena sativa*) - RO; redroot pigweed (*Amaranthus retroflexus*) - PW; mustard (*Brassica juncea*) - MD; curly dock (*Rumex crispus*) - CD; and hairy crabgrass (*Digitaria sanguinalis*) - CG.

After treatment, the flats are placed in the greenhouse at a temperature of 70° to 85° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete kill.

POST-EMERGENCE HERBICIDE SCREENING TEST

Seeds of six plant species, including hairy crabgrass (CG), watergrass (WG), red oat (RO), mustard (MD), curly dock (CD) and Pinto beans (*Phaseolus vulgaris*) (BN), are planted in the flats as described above for pre-emergence screening. The flats are planted in the greenhouse at 70° to 85° F. and watered daily with a sprinkler. About 10 to 14 days after planting, when the primary leaves of the bean plants are almost fully expanded and the first trifoliate leaves are just starting to form, the plants are sprayed. The spray is prepared by weighing out 20 mg. of the test compound, dissolving it in 5 ml. of acetone containing 1% Tween 20 ® (polyoxyethylene sorbitan monolaurate) and then adding 5 ml. of water. The solution is sprayed on the foliage using an atomizer at an air pressure of 5 lb./sq. inch. The spray concentration is 0.2% and the rate is 8 lb./acre. The spray volume is 476 gallons per acre.

The results of these tests are shown in Table II.

applied in a variety of ways at various concentrations. In practice, the compounds are formulated with an inert carrier, utilizing methods well known to those skilled in the art, thereby making them suitable for application as dusts, sprays, or drenches and the like, in the form and manner required. The mixtures can be dispersed in water with the aid of a wetting agent or they can be employed in organic liquid compositions, oil and water, water in oil emulsions, with or without the addition of wetting, dispersing or emulsifying agents. An herbicidally effective amount depends upon the nature of the seeds or plants to be controlled and the rate of application varies from 0.10 to approximately 50 pounds per acre. The concentration of a compound of the present invention, constituting an effective amount in the best mode of administration in the utility disclosed, is readily determinable by those skilled in the art.

The phytotoxic compositions of this invention employing an herbicidally effective amount of the compound described herein are applied to the plants in the conventional manner. The present invention contemplates methods of selectively killing, combatting or controlling undesired plants which comprises applying to at least one of (a) such weeds and (b) their habitat, that is, the locus to be protected, and herbicidally effective or toxic amount of the particular active compound alone or together with a carrier or adjuvant. Thus, the dust and liquid compositions can be applied to the plant by the use of power dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles and these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface

TABLE II

| COMPOUND NUMBER | HERBICIDAL ACTIVITY - SCREENING RESULTS Per Cent Control at 8 lb./A. | | | | | | | | | | | | |
|---|---|---|---|---|---|---|---|---|---|---|---|---|
| | Pre-emergence | | | | | | | Post-emergence | | | | | |
| | CG | FT | WG | RO | MD | CD | PW | CG | WG | RO | MD | CD | BN |
| 1 | 79 | 98 | 100 | 98 | 100 | 50 | 40 | 90 | 90 | 60 | 80 | 100 | 70 |
| 2 | 80 | 60 | 50 | 0 | 0 | 0 | 0 | 20 | 20 | 0 | 20 | 20 | 0 |
| 3 | 90 | 90 | 90 | 50 | 10 | 10 | 0 | 70 | 70 | 40 | 0 | 50 | 60 |
| 4* | 10 | 10 | 20 | 30 | 100 | 30 | 0 | 98 | 20 | 0 | 0 | 0 | 10 |
| 5* | 95 | 10 | 10 | 10 | 0 | 0 | 0 | 100 | 40 | 0 | 98 | 80 | 10 |
| 6 | 100 | 100 | 98 | 100 | 20 | 10 | 10 | 80 | 70 | 60 | 50 | 50 | 70 |
| 7 | 10 | 10 | 80 | 10 | 0 | 0 | 0 | 70 | 70 | 0 | 0 | 0 | 50 |
| 8 | 99 | 99 | 100 | 90 | 80 | 0 | 0 | 90 | 80 | 80 | 60 | 0 | 30 |
| 9 | 100 | 98 | 100 | 98 | 70 | 50 | 30 | 90 | 90 | 70 | 50 | 0 | 0 |
| 10* | 90 | 0 | 95 | 0 | 0 | 0 | 0 | 95 | 40 | 0 | 90 | 0 | 0 |
| 11 | 95 | 95 | 95 | 0 | 30 | 10 | 0 | 80 | 40 | 0 | 90 | 70 | 0 |
| 12 | 100 | 98 | 95 | 95 | 100 | 50 | 30 | 98 | 90 | 30 | 100 | 60 | 0 |
| 13 | 90 | 90 | 80 | 70 | 30 | 10 | 0 | 40 | 70 | 10 | 70 | 40 | 0 |
| 14 | 90 | 95 | 95 | 90 | 100 | 30 | 10 | 40 | 80 | 10 | 50 | 80 | 40 |
| 15 | 100 | 95 | 95 | 80 | 95 | 80 | 40 | 90 | 80 | 40 | 100 | 80 | 20 |
| 16 | 80 | 80 | 70 | 10 | 0 | 0 | 0 | 90 | 80 | 10 | 100 | 0 | 20 |

*Screening Results - per cent control at 20 lb/A pre- and post-emergence.

The compounds of the present invention are used as pre-emergence or post-emergence herbicides and are of the soil by conventional means such as discing, dragging or mixing operations.

The phytotoxic compositions of this invention can also contain other additaments, for example, fertilizers, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof; triazine derivatives, such as 2,4-bis(3-methoxypropylamino)-6-methyl-thio-s-triazine; 2-chloro-4-ethylamino-6-isopropylamino-s-triazine, and 2-ethylamino-4-isopropylamino-6-methyl-mercapto-s-triazine, urea derivatives, such as 3-(3,4-dichlorophenyl)-1,1-dimethyl urea and acetamides such as N,N-diallyl-α-chloroacetamide, N-(α-chloroacetyl)-hexamethyleneimine, and N,N-diethyl-α-bromoacetamide, and the like; benzoic acids such as 3-amino-2,5-dichlorobenzoic; and thiocarbamates, such as S-propyl dipropylthiocarbamate; S-ethyldipropylthiocarbamate; S-ethyl hexahydro-1H-azepine-1-carbothioate and the like. Fertilizers useful in combination with the active ingredients include, for example, ammonium nitrate, urea and superphosphate. Other useful additaments include materials in which plant organisms take root and grow, such as compost, manure, humus, sand and the like.

Various changes and modifications are possible without departing from the spirit and scope of the invention described herein and will be apparent to those skilled in the art to which it pertains. It is accordingly intended that the present invention shall only be limited by the scope of the claims.

What is claimed is:

1. The method of preparing acyclic and alicyclic N-substituted halo-2-pyrrolidinones of the formula

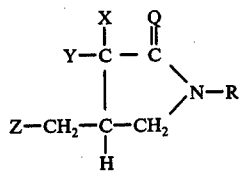

in which R is lower alkyl, haloalkyl, alkenyl, cycloalkyl, cycloalkylalkyl, benzyl and chlorobenzyl; X is hydrogen or chlorine; Y is chlorine or bromine, and Z is chlorine or bromine; which comprises the steps of heating an N-alkenyl halomethyl amide of the formula

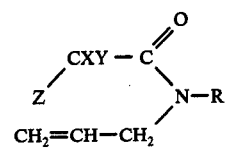

in which R, X, Y and Z are as above-defined, in the presence of a catalytic amount of ferrous ion and recovery of the resulting product.

2. The method of claim 1 in which said reaction is carried out at a temperature of between about 50° C. and about 190° C.

3. The method of preparing acyclic and alicyclic N-substituted halo-2pyrrolidinones of the formula

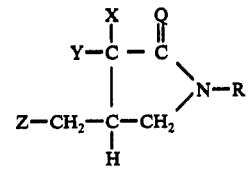

in which R is lower alkyl, haloalkyl, alkenyl, cycloalkyl, cycloalkylalkyl, benzyl and chlorobenzyl; X is hydrogen or chlorine; Y is chlorine or bromine, and Z is chlorine or bromine; which comprises the steps of heating an N-alkenyl halomethyl amide of the formula

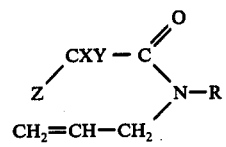

in which R, X, Y and Z are as above-defined, in the presence of a catalytic amount of ferrous ion in the presence of a high boiling solvent and recovery of the resulting product.

4. The method of claim 3 in which the ferrous ion catalyst source is selected from ferrous chloride, ferrous bromide, iron metal, ferrocene, and ferrous acetonyl acetonate.

5. The method of claim 3 in which said reaction is carried out at a temperature of between about 50° C. and about 190° C.

6. The method of claim 5 in which the compound wherein R is allyl, X is hydrogen, Y is chlorine and Z is chlorine is prepared from

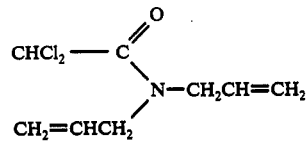

by heating in the presence of diethylene glycol dimethyl ether.